United States Patent
Ky

(10) Patent No.: US 9,797,722 B1
(45) Date of Patent: Oct. 24, 2017

(54) MINI 3D ORIENTATION SENSOR

(71) Applicant: Albert Ky, Alemeda, CA (US)

(72) Inventor: Albert Ky, Alemeda, CA (US)

( * ) Notice: Subject to any disclaimer, the term of this patent is extended or adjusted under 35 U.S.C. 154(b) by 0 days.

(21) Appl. No.: 15/230,461

(22) Filed: Aug. 7, 2016

(51) Int. Cl.
*G01C 19/02* (2006.01)
*G08B 21/04* (2006.01)

(52) U.S. Cl.
CPC .......... *G01C 19/02* (2013.01); *G08B 21/043* (2013.01); *G08B 21/0415* (2013.01); *G08B 21/0423* (2013.01)

(58) Field of Classification Search
CPC .. G01C 19/02; G08B 21/043; G08B 21/0423; G08B 21/0415
USPC ............ 324/691; 340/539.1, 539.11, 539.12, 340/539.13, 573.7
See application file for complete search history.

(56) References Cited

U.S. PATENT DOCUMENTS 9,163,498 B2 * 10/2015 Cairns ............... E21B 47/02232
2003/0204962 A1 * 11/2003 Mangerson .............. G01C 9/06
33/366.15

* cited by examiner

*Primary Examiner* — Jermele H Hollington
*Assistant Examiner* — Kristopher Yodichkas
(74) *Attorney, Agent, or Firm* — Patent Alchemy

(57) ABSTRACT

The Mini 3D orientation sensor device has convex spherical body structure in a mechanical sensor coupled to logic to manage the reverse touchscreen component, alarm and other functions for the sensor. The spherical housing sensor is comprises a plurality of layers analogous to a touchscreen complete with conducting probes, an unconstrained surface compressing ball dynamic inside the spherical grid position structure that closes a electric circuit upon depressing the inside surface of the sphere housing. The sphere depressed coordinates are mapped to its 3D orientation upon output.

8 Claims, 10 Drawing Sheets

Sensor and RFID tag Connection

MINI 3D ORIENTATION SENSOR

CROSS-REFERENCE TO RELATED APPLICATION

U.S. Pat. No. 8,941,490, filed Mar. 8, 2013, is incorporated by reference herein in its entirety.

BACKGROUND

Field of the Invention

The present invention generally relates to wrist mounted life alarm dialers and more specifically, to devices with passive or non-conscious triggering of life saving requests for help in the event of user loss of consciousness.

From time to time life threatening events that occur from sudden loss of consciousness, to severe trauma and sudden paralysis or loss of strength, can render the victim with an inability to activate an alarm for help. While this is not always necessary when others are proximate and can act to save a life, this is not always the outcome and the consequences are permanent.

There are currently some solutions in the market place in the way of wrist phones and wearable wrist devices. These generally alert the user when their time has elapsed, timer types alarms, and can call multiple calling numbers. They also provide the capability for the user to communicate with the helping party through voice or text. But at the very moment that the user is supposed to push the button to trigger the alarm, if wearer becomes suddenly incapacitated, then the price can be infinite, as it could cost a life.

Hence what is needed are devices that have intelligence to alert rescue personnel upon user loss of capacity to act or move. Low power electro-mechanical sensors are needed to ascertain the continuous changes of the orientation of the sensor, which in turn determines the continuous and instantaneous position of movements of a wrist upon which it rests.

The field of sensor technology is increasing offerings of mostly solid state sensor and devices. But there is a nitch for small electro-mechanical devices where power consumption is low or can be produced by mechanical means. What is needed are orientation and movement sensor technology which does not have the limitations of strictly electronic devices.

SUMMARY

The present invention discloses a 3D spherical shaped resistive touchscreen integrated into a mechanical orientation sensor device. The device comprises two flexible sheet conducting layers formed into a spherical configuration and coated with a resistive material separated by an air gap or microdots with each conducting sheet layer having striped electrode lines on substrates such as glass or plastic, electrode surfaces facing each other with conducting filament lines more or less perpendicular forming a grid where superimposed on each other each having a separate chargeable circuits. An internal placed unconstrained ball with weight sufficient to place into contact the conducting layer circuits upon ball's physical contact on the internal sphere surface causing contacting conducting sheets providing closed circuits switch on voltage gradient discharge from the first end of the conducting layers into the contacting line fiber of the second conducting layer establishing a new resistance or voltage drop. The second layer circuit with time delay discharges and the second layer circuit resistance is read providing two measured resistances representing the coordinate location of the ball inside the sphere sensor. A processor and logic coupled to the sensor maintains potential on the two conducting layers and control management functions for alarms and circuitry I/O for tracking, such that the ball impinging on the inside layer, causing circuit resistance changes from the point of contact followed by a circuit potential switch to the other conducting layer. A subsequent second layer voltage discharge changes the second layer circuit resistance and provides the second dimension of the ball position coordinate. Therefore the two crossing circuit loop resistance changes represent the coordinate location of the contacting ball inside the sphere sensor and registers the ball location data in the logic for processing, whereby at the point of contact, the voltage will be diverted from the x layer into the corresponding filament of the y layer revealing the y coordinate and reversing the discharge to obtain the x coordinate, analogous to a touchscreen but with accommodations to the spherical curvature and the small size.

BRIEF DESCRIPTION OF DRAWINGS

Specific embodiments of the invention will be described in detail with reference to the following figures.

DETAILED DESCRIPTION

Figure 1:
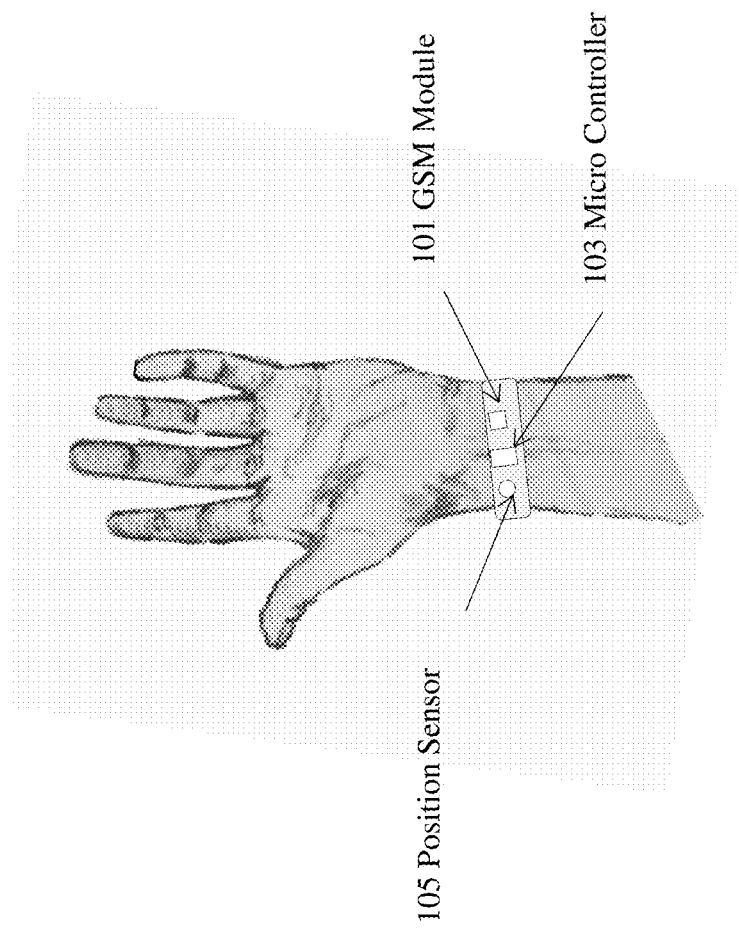
FIG. 1 illustrates the basic mechanical geodesic movement sensor with accompanying electronics on a wristband according to an embodiment of the present invention.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Objects and Advantages

The present invention discloses an electro-mechanical orientation sensor. Accordingly, it is an object of the present invention to use cessation of human movement for a preset designated duration as signal of a life in jeopardy.

Activity generally indicates signs of life. It is the observation of the applicant that the wrist of a human being is the most active external part of the human body, as far as voluntary muscles are concerned. During awake periods, absent medication or illness, the wrist of a human body intermittently makes some spontaneous movements. The cessation of such spontaneous movements, exceeding a given period of time, may represent a warning sign that something is wrong inside that body and needs attention. Under such a case, if a aural stimulus can not make that person to react, an alarm call should alert the appropriate parties.

Another object of the present invention is to have a timer switch in conjunction with a sensor wearer of a body sensor to process the positions sensed from a body movement or lack of movement. To determine that a wearer's wrist is not moving, one has to find that it has not changed position or orientation for a period of time. To determine a change or not of a body's physical movement, a mechanism through the body sensor is required to monitor a body's position and orientation continuously. Unchanged position periods exceeding a preset limit will automatically trigger an aural signal, urging the user of the life alarm sensor to make a movement toward a conscious response or emit a call for help.

Another object of the invention is to eliminate any magnetic interference from the sensor, for the position sensor to be incorporated into the main bracelet. Yet another object of the invention is to eliminate sharp edges creating corners retarding sphere movement in the movement orientation sensor. Still another object of the invention is a hybrid mechanical movement sensor, with reduced power consumption.

Embodiments of the Invention

In an aspect of the invention, absence of physical movement from an individual wearing a body mechanical sensor is detected upon a circuit closing and staying closed for a given period. After a preset period an aural alarm is triggered, with a clock continuing to run. After a second preset period, a timer switch automatically triggers a wireless network or GSM autodialer to alert pre-designated parties.

In an embodiment of the invention, a body attached mechanical sensor is worn on the internal side of the wrist, the timer switch and the GSM autodialer is worn on the internal side at a length away to avoid any interference from the sensor.

FIG. 1 illustrates the basic mechanical internal movement sensor with accompanying electronics on a wristband according to an embodiment of the present invention. In an embodiment of the invention the geodesic. The position sensor 105 is shown placed serially adjacent and electrically coupled to the micro controller 103 which is electrically coupled to the GSM module 101 sharing a wristband base. In an embodiment of the invention, the mechanical sensor is a 3D spherical shape comprised reverse touch screen which contains an unconstrained ball freely moving about on the inside surface of the sphere sensor. The ball's weight or force on the inside sphere sensor surface is sufficient to produce a closed circuit which identifies the balls position on the sphere and hence the orientation.

Figure 2:
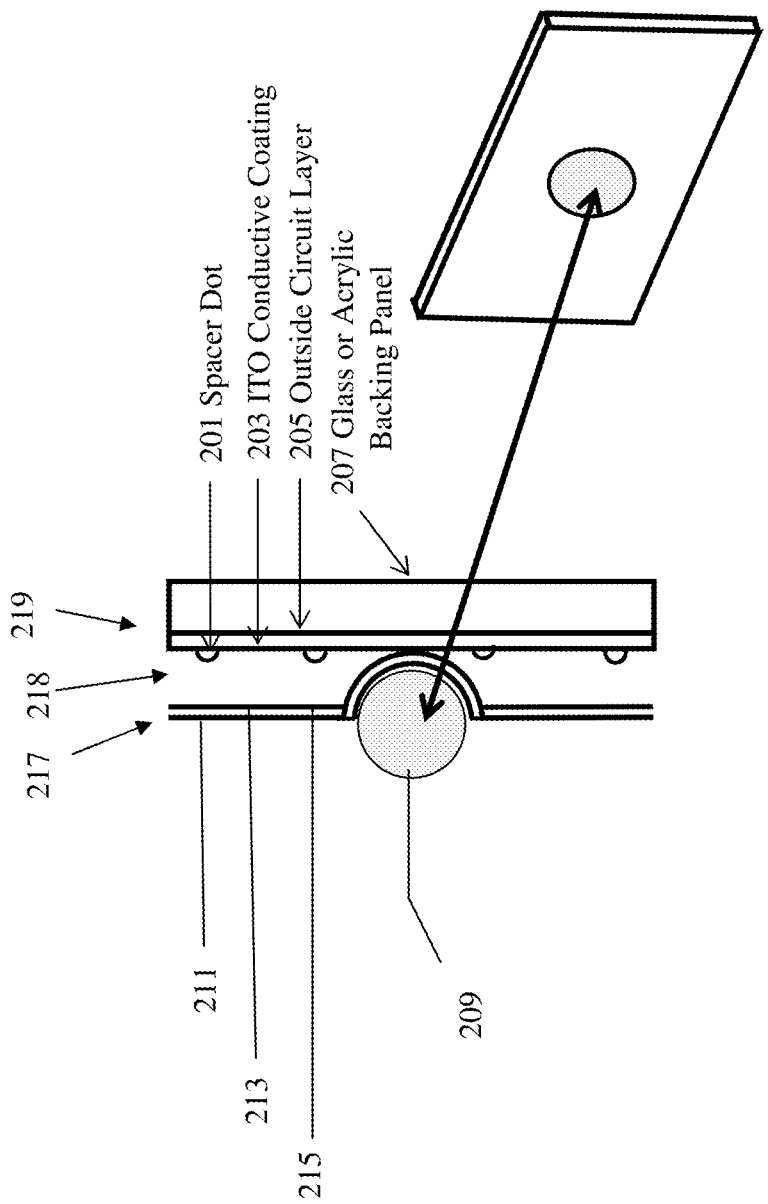
FIG. 2 illustrates the resistive circuit layer construction of the sensor housing in an embodiment of a mini 3D orientation sensor.

FIG. 2 illustrates a spherical resistive touchscreen component in an embodiment of the invention. Two flexible sheets 217 219, inside 217 and outside 219 are coated with a resistive material and separated by an air gap 218 or microdots 201 are placed in proximity to each other. Each sheet has striped electrodes on substrates such as glass or plastic, and face each other. When these two sheets having parallel electrode conductor lines are positioned perpendicular with each other, and are pushed together to make contact, a conduction voltage will register the precise location of the contact coordinate represented by the conducting layer grid on each sheet.

The outside sheet will typically have spacer dots 201 coupled to an oxide conductive coating 203 layered on a circuit layer 205 supported on a glass or acrylic backing panel layer 207. Facing the outside sheet 219 will be an inside sheet 217 having a conductive coating 215, could be made of Indium Tin Oxide, ITO, a transparent conducting oxide, easy to deposit on surface or other conducting oxide, adhering to an inside circuit layer 213 which itself is coupled to a PET film 211, polyethylene terephthalate. Antimonium Tin Oxide, ATO, another conducting oxide, can be used as a conductive coating. A contact making ball 209 provides the contact making object, where it rolls depresses the two sheets into making contact.

A resistive touchscreen uses two ATO conductive layers: x grid of micro conductive filament and y grid of micro filament. These two layers, inside 217 and outside 219, and are superimposed one on the other separated by separator or spacer dots 201. The spacer dots 201 are rigidly coupled to a conductive coating 201A pressure exerted on the sphere inside surface will place these two layers in contact at the pressure point. A voltage gradient is discharged from one end of one of these layers, eg. x layer. Where the ball depresses the sheets to make contact between the resistive circuit layers, a switch is closed providing the coordinate of the contact location. At the point of contact, the voltage will be diverted into the corresponding filament of the other layer, eg. y layer. Using the same method on the y layer, the coordinate on the x axis is found. So, the ball inside a spherical surface impinging coordinate on the sphere inside surface is thus data defined by the x and y coordinate. These coordinates give us the location of the pressure point in the sphere. The mechanism function is the similar as that of a resistive touch screen, but the construction of the sphere housing analogous to a touchscreen must make accommodations to the spherical curvature and the small size.

Figure 3:
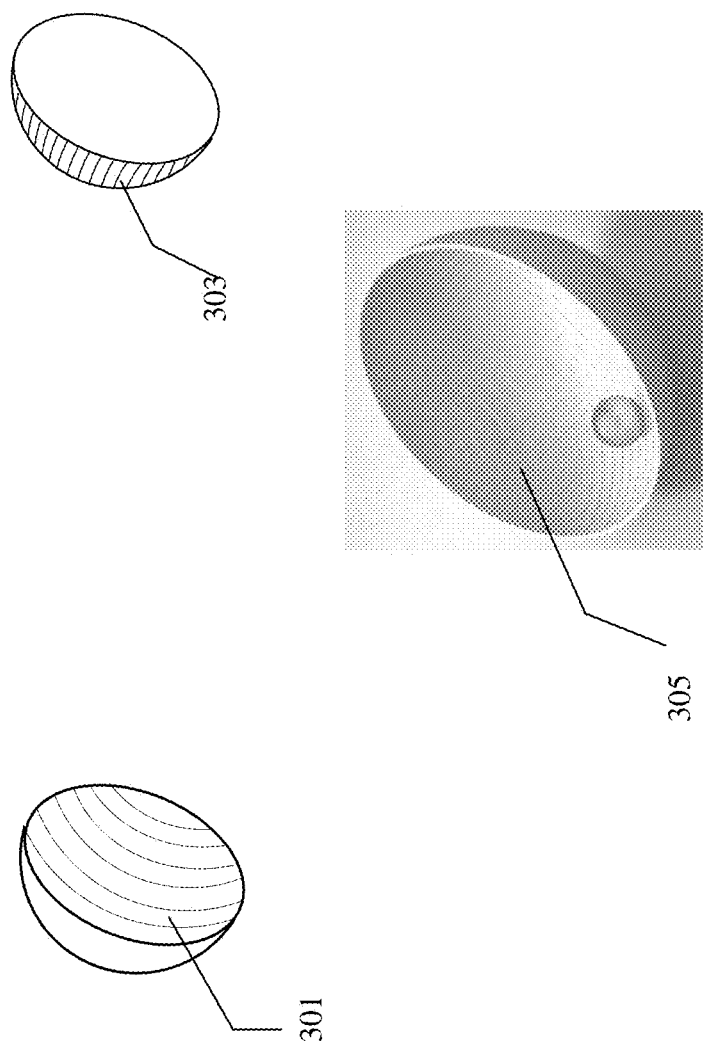
FIG. 3 illustrates conductive layer formed in a spherical shaped construction in an embodiment of a mini 3D orientation sensor.

FIG. 3 illustrates conductive layer formed in a spherical shaped construction in an embodiment of a mini 3D orientation sensor.

Figure 6:
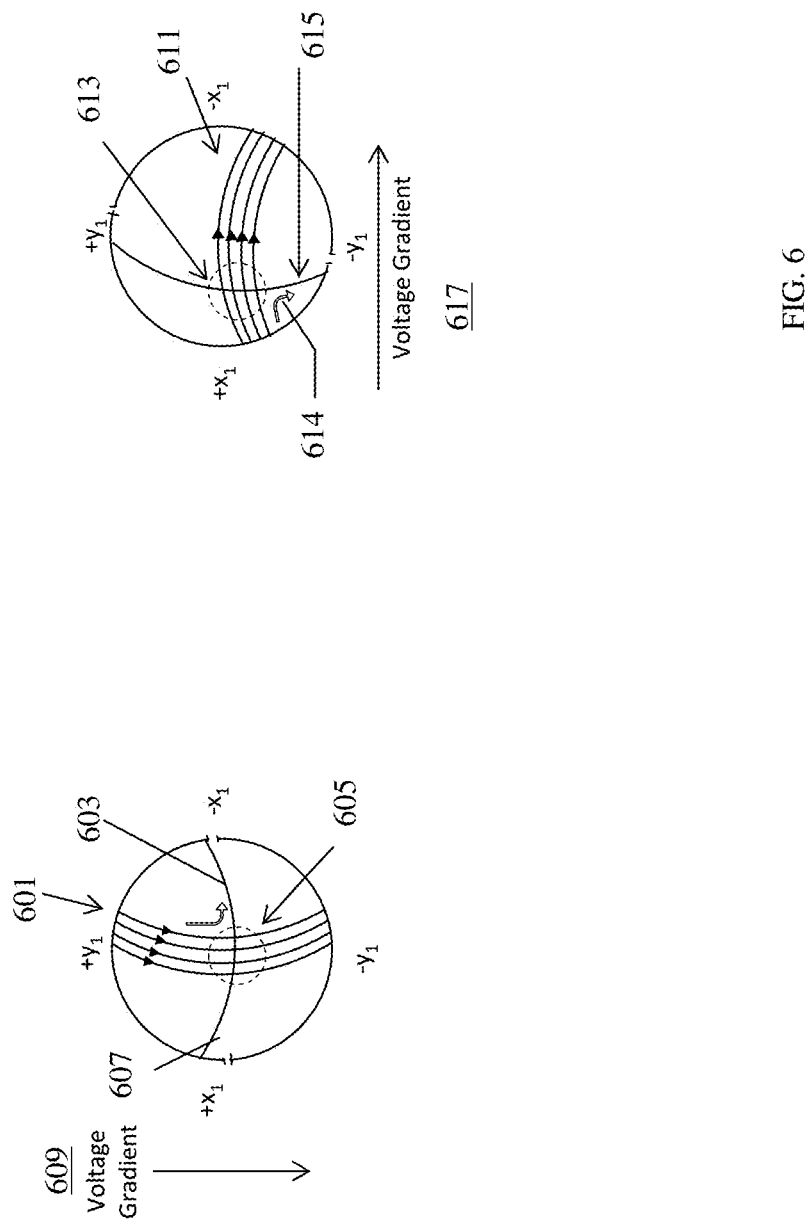
FIG. 6 illustrates an electrical grid coordinate configuration for spherical shaped construction in an embodiment of a mini 3D orientation sensor.

Two basic electrical grid layers of the touchscreen are fused or combined into hemispheric shaped objects for the conduction layers of the touchscreen housing: parallel latitude-line shaped hemispheres 301 for x grid and parallel longitude-line shape layer 303 for y grid or vice versa. (FIG. 6). These could be in ATO, ITO or other such conductive material The latitude-lined 301 and the longitude-lined hemisphere conductive layers are then superimposed on each other to form a conductive layer electrical grid in the form of a micro-dome. The dome 305 will contain a free rolling baring with layer impinging force.

Figure 4:
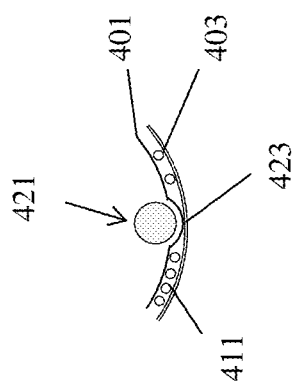
FIG. 4 displays a cross section view of a spherical shaped construction in an embodiment of a mini 3D orientation sensor.
Figure 4:
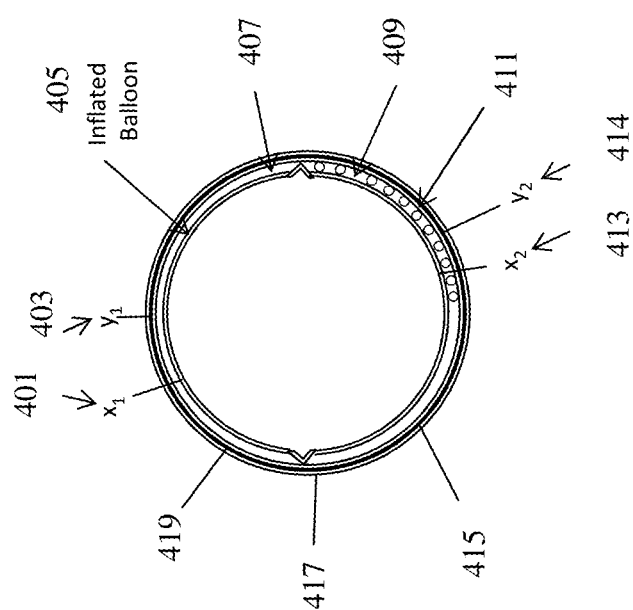

FIG. 4 displays a cross section view of a spherical shaped construction in an embodiment of a mini 3D orientation sensor. Just inside adjacent to an outer shell 417 of a sensor is a conductive layer with parallel conducting fibers 419 415 for one axis of a spherical grid and a separate layer of conducting fiber bands 407 409 of an orthogonal axis incorporated in the spherical shaped sensor. Evenly interspersed separator nodes 411 isolate the two conducting layers 401 403 from each 413 414 other respectively. The conduction layers can be of ITO, ATO or other material with electrical conduction properties having malleable or conforming mechanical properties to form a small sphere.

An electrical potential is maintained between the layers where upon any contact between these layers will cause current to flow through a completed circuit to a microcontroller or voltage registering device. A metal ball or free rolling object 421 with sufficient mechanical advantage to bend the inside conduction 401 layer to make contact 423 with the outside conducting layer 403 will complete an electrical circuit identifying the spherical coordinate $X_1, Y_1$ or $\theta_1, \phi_1$ spherical coordinates registering the precise location of the layer contact forcing metal ball object inside the spherical housed sensor. An additional inside supportive layer 405 stays rigidly adjacent to the inside conducting layer 407 and maybe held firmly through adhesion or internal pressure. The most inner supportive layer 405 must be bendable sufficient to allow a metal ball object 421 to force an electrical contact 423 between the two opposite conduction layers 401 403

Figure 5:
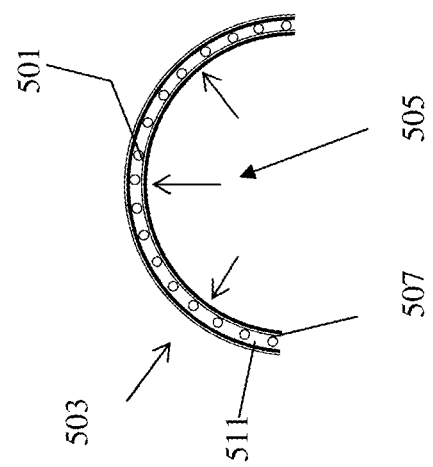
FIG. 5 displays a cross section view of an internal layer support in a spherical shaped construction in an embodiment of a mini 3D orientation sensor.

FIG. 5 displays a cross section view of an internal layer support in a spherical shaped construction in an embodiment of a mini 3D orientation sensor. In order to maintain compressive support for a the internal conduction layer additional compression support layer is added inside the sphere sensor to hold the inner layer in place. This may be done through a pressurization 505 of a very thin flexible balloon layer wherein a metal ball object is allowed to freely roll with each rotation of the sphere. As in other embodiments the inner conduction layer 507 is isolated from the outer conduction layer 511 by a separator node layer 501. These are all integrated into an outer rigid sphere layer 503 to protect and insolate the sensor.

FIG. 6 illustrates an electrical grid coordinate configuration for spherical shaped construction in an embodiment of a mini 3D orientation sensor.

At least two different types of conductive layer embodiments may be uses. In the Matrix type embodiment, striped electrodes 601 611 on substrates such as glass or plastic face each other. The conducting layer wire or filament array cross over positions represent grid points on the sphere sensor. In the Analogue conducting layer embodiment, transparent electrodes without any patterning facing each other. When contact is made to the surface of the sphere inside layer touchscreen 605 613, the two conducting sheets are pressed together. On these two sheets there are latitudinal 611 and longitudinal lines 611 that, when pushed together at intervals respectively, register the precise location of the ball 605 613.

FIG. 6 illustrates a matrix type conducting layer embodiment. During operation of a multi-wire touchscreen mechanism inside a spherical orientation sensor, a uniform, unidirectional voltage gradient 609 is applied to the longitudinal conducting 601 layer. When the two mutually perpendicular layers meet at the latitude line 603 607 are depressed with contact, the latitudinal layer 614 provides the identifying voltage as distance along the longitudinal layer, providing the X or theta coordinate. When this contact coordinate has been acquired, the voltage gradient 617 is applied to the latitudinal layer 611 to ascertain the Y or phi coordinate. These operations occur in sequence within milliseconds, registering the exact ball location 613 605 as contact on the inside of the spherical orientation sensor grid is made. The X, Y or Phi, Theta coordinates then represent the location of a metal ball in the spherical sensor. Note are the latitude line array 601 and longitude line array 613 electrically coupled to managing ICs and logic comprising the timer switch, wireless network dialer, wireless network, and others. In an embodiment of the invention the longitudinal and latitudinal conduction arrays may have variable grid point configuration.

Contacting conducting layers provide closed circuits to switch on voltage gradient discharge from the first end of the conducting layers into the contacting line fiber of the second conducting layer establishing a new resistance or voltage drop. The second layer circuit with time delay discharges and the second layer circuit resistance is read providing two measured resistances representing the coordinate location of the ball inside the sphere sensor. Integrated Circuits (IC), processor and logic are coupled to the sensor maintaining voltage and timing on the two conducting layers and control management functions for alarms and IC I/O.

Figure 7:
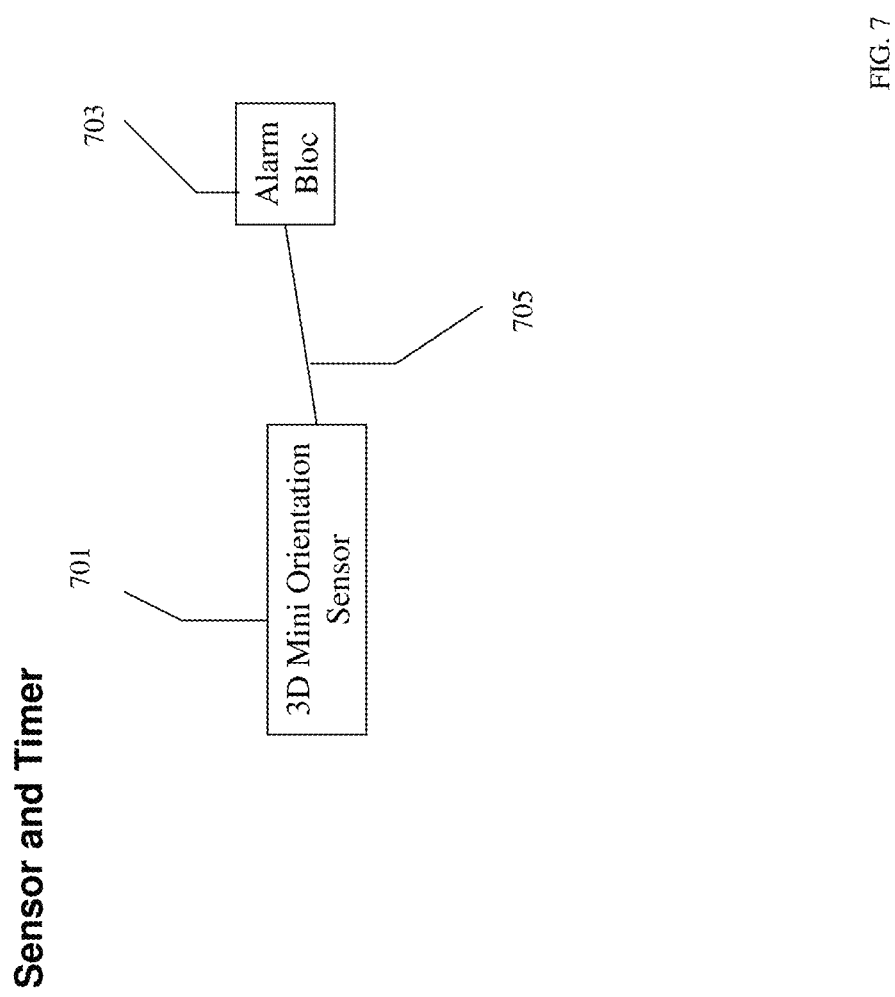
FIG. 7 shows a high level schematic diagram of a 3D orientation sensor coupled to an automatic life alarm in accordance with an embodiment of the present invention.

FIG. 7 shows a high level schematic diagram of a 3D orientation sensor coupled to an automatic life alarm in accordance with an embodiment of the present invention. An orientation sensor attached to a wearer's wrist 701 senses for cessation of movement and final orientation, transmits a signal by wire or wireless 705 protocol to the alarm circuitry 703.

Figure 8:
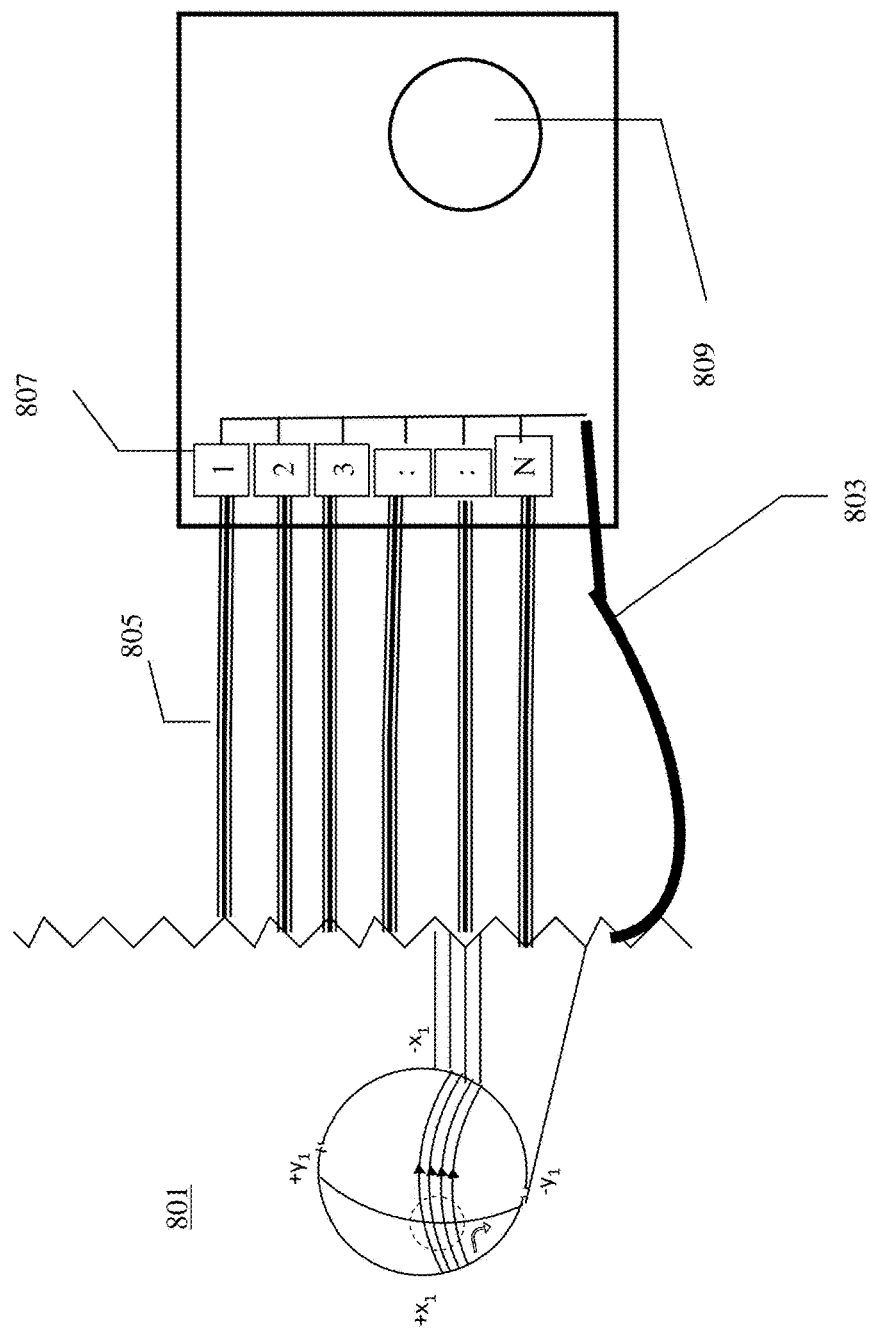
FIG. 8 illustrates a 3D mini orientation sensor 801 with an alarm in accordance with an embodiment of the present invention.

FIG. 8 illustrates a 3D mini orientation sensor 801 with an alarm in accordance with an embodiment of the present invention. This embodiment contains an electrical internal touch sensitive sensor 801 and electrical leads 805 to the timer switch 807. An electrically conducting ball freely rolling in the interior of the sensor closed convex interior from any movement of the wrist or wearer will position itself on grid point. Upon cessation of body movement, the electrically sensitive sphere will fall under gravity onto the lowest gravity oriented level of the sensor and make electrical circuit contact in one of the contact sensitive intersections, thus closing the circuit ground 803 of a particular point and energizing the circuit and producing signal. The alarm and other circuits will require power 809 which can be battery or other compact available mobile power source.

From the time that the timer switch is closed to a preset wait period following the timer start, the timer will run and upon elapse of time emit an aural alarm. More than one preset time can be selected. In an embodiment of the invention, a first preset period can signal for the aural emission of a local sound alarm to awaken the user-wearer to make movement with the wrist. If upon the aural alarm the sphere continues to rest on the same plate, indicating no physical response from the user-wearer, the timer switch will initiate a Wireless Network autodialer for help from local parties, meanwhile transmitting the GPS position if available. Any wireless networks can be used including GSM, CDMA, TDMA, WiFi, and other wireless protocols.

The orientation sensor can have different configurations of conduction grids. A 36 grid point sensor embodiment performs substantially similar to a 12 grid point sensor, as to the free conducting sphere and connecting circuits. The advantage of the 36 grid point sensor is that it is more sensitive to small and slow movements of the wrist and better for less active individuals.

Figure 9:
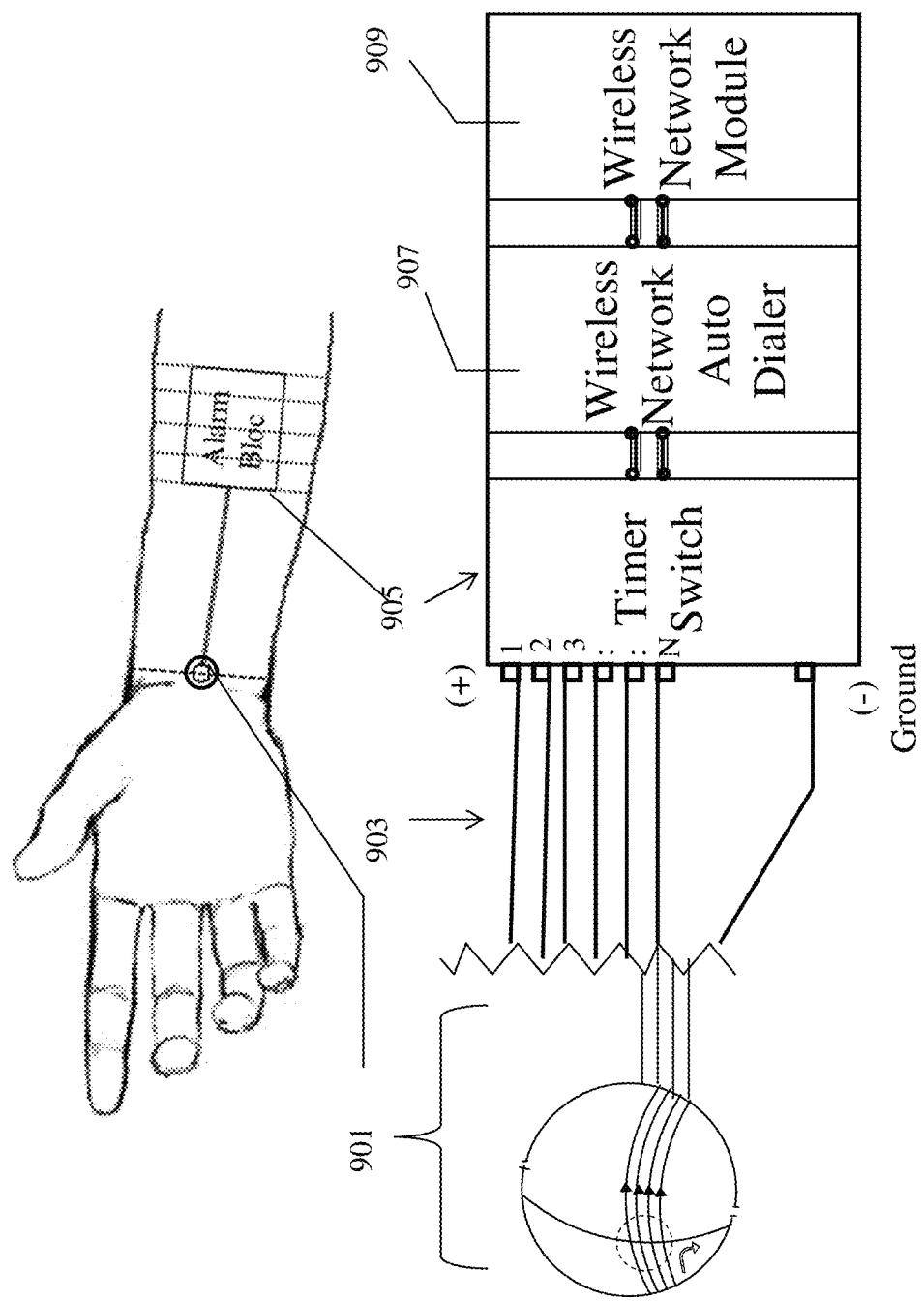
FIG. 9 illustrates a wrist mounted dodecahedron orientation sensor 901 alarm circuitry 905 in accordance with an embodiment of the present invention.

FIG. 9 illustrates a wrist mounted spherical orientation sensor 901 alarm circuitry 905 in accordance with an embodiment of the present invention. Electrical leads 903, from conducting layer grid positions shown connects to the positive lead in the timer switch 905 circuitry. The Alarm bloc contains the timer switch, wireless network autodialer 907 and the wireless network module 909 and is also shown worn on the user's wrist.

Figure 10:
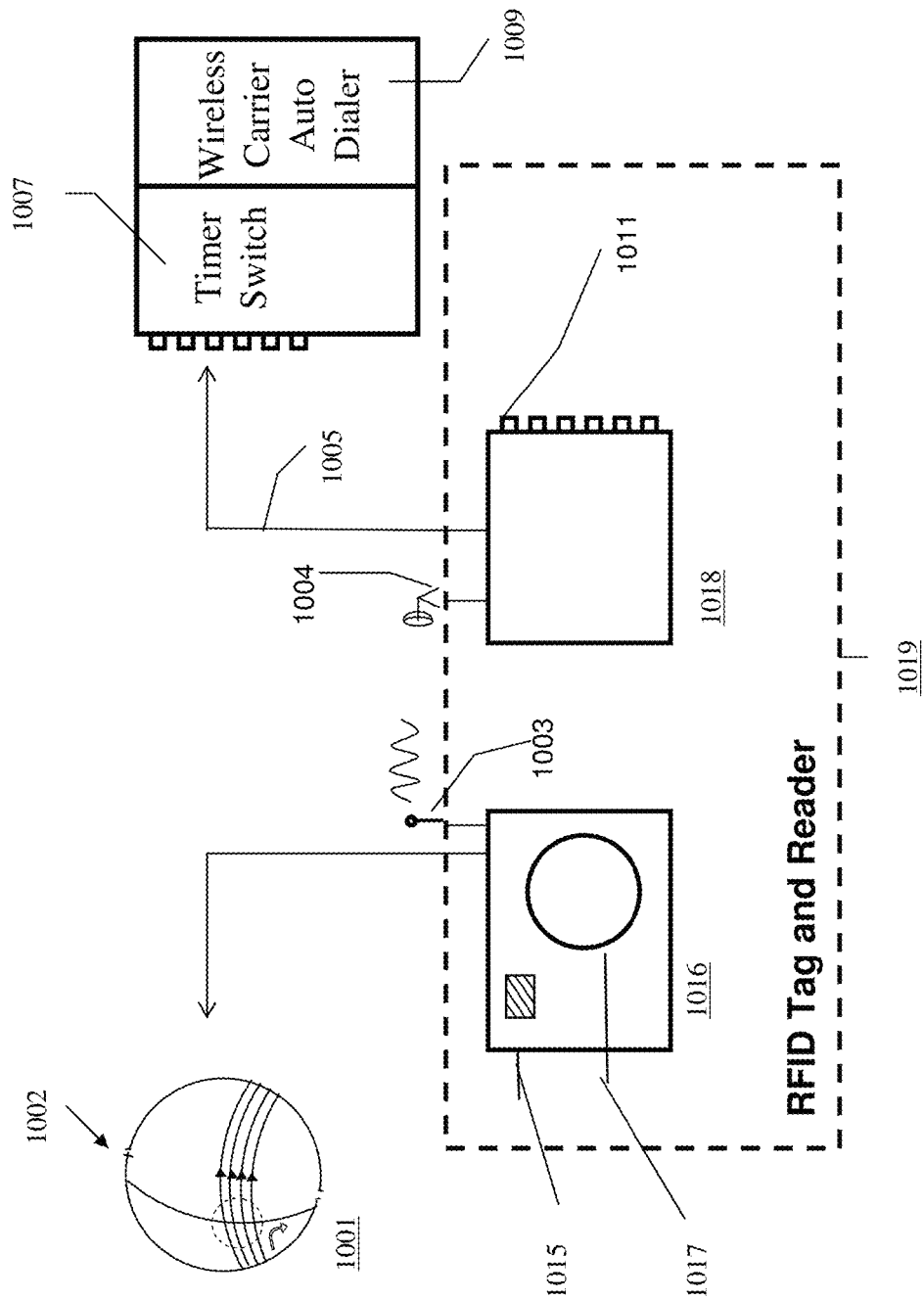
FIG. 10 illustrates a 3D mini orientation sensor with distributed alarm circuitry using RFID in accordance with an embodiment of the invention.

FIG. 10 illustrates a 3D mini orientation sensor 1011 with distributed alarm circuitry 1007 1009 using RFID 1019 in accordance with an embodiment of the invention. In this embodiment an RFID tag containing the chip 1015 and battery 1017 are operatively coupled 1003 to the sensor 1002 electrical circuitry. The RFID tag 1016 coupled 1003 1004 to the reader 1018 and reader 1018 to the timer 1007 can be of typical RFID communication 1005 or other wireless protocol. The grid position points shown is connected to tags 1016 each of bus points in a chip 1015, identifying the position with of a different frequency or transmitted grid coordinate of the sensor. Each frequency represents a unique grid position and upon a grid position circuit identified the energized circuit will respond to transmit the grid position and hence the sensor orientation. In another embodiment the Integrated Circuit (IC) chips can be integrated into one multiple interchangeable code RFID tag.

The circuit of each of the IC chips is open, leaving exposed positive and negative ends. The negative ends of all the ICs are connected ground, to the negative lead of the sensor 1002, which is itself connected to all the peripheral strips. The positive leads are frequency matched to the reader 1018 each by grid position to frequency 1011. The wrist movement of the sensor is disconnected from the timer switch though the RFID 1019 system, tag 1016 and reader 1018.

In the semi-sphere cup grid position embodiment the positive lead of each IC is connected to the central strip of two cups opposite each other. As the conducting ball falls into a hemisphere, it will connect the conducting layers closing the circuit between and mapping location to IC logic. If the Radio Frequency Identification (RFID) tag 1016 transmits a code frequency to the RFID reader, it will do so at the code frequency of the closed circuit IC revealing it's position and orientation. When the ball rolls into another grid point, the logic 1016 will again emit the code frequency of its mapped cup and therefore orientation.

In an embodiment of the invention, the RFID reader 1018 is connected to the timer switch 1007. Each time the reader receives a code frequency or grid position 1011 from the point 1016, it passes it to the timer switch 1007 for processing. The RFID tag 1016 is programmed to transmit a code frequency every 2 minutes to the timer switch 1007 which will receive a code frequency every 2 minutes from the reader 1018. The timer switch 1007 is programmed to count consecutive RFID reader transmissions, and counting the same frequency code 7 consecutive times indicates that the same cup, has had the ball for 14 minutes.

This indicates body sensor inactivity and inactivity directs the alarm to emit a loud aural signal to alert the user to move. If the timer switch 1007 receives the same frequency code the $8^{th}$ time, that means 16 minutes of no movement of the wrist, the timer switch 1007 will trigger the wireless carrier autodialer 1009 to alert a monitoring room and rescue or emergency responder parties.

Therefore, while the invention has been described with respect to a limited number of embodiments, those skilled in the art, having benefit of this invention, will appreciate that other embodiments can be devised which do not depart from the scope of the invention as disclosed herein. Other aspects of the invention will be apparent from the following description and the appended claims.

What is claimed is:

1. A mini 3D spherical shaped resistive touchscreen integrated into a mechanical orientation sensor device comprising:
    two flexible sheet conducting layers formed into a spherical configuration and coated with a resistive material separated by an air gap or microdots;
    each conducting sheet layer having an array of electrode conductor lines on substrates, electrode surfaces facing each other with conducting filament lines are more or less perpendicular forming a grid where superimposed on each other;
    an internal placed unconstrained ball with weight sufficient to place into contact the conducting layer circuits upon ball's physical contact on the internal sphere sensor surface;
    contacting conducting sheets providing closed circuits switch on voltage gradient discharge from the first end of the conducting layers into the contacting line fiber of the second conducting layer establishing a new resistance or voltage drop;
    the second layer circuit with time delay discharges and the second layer circuit resistance is read providing two measured resistances representing the coordinate location of the ball inside the sphere sensor;
    processor and logic coupled to the sensor maintaining voltage on the two conducting layers and control management functions for alarms and circuitry I/O;
    the ball impinging on the inside layer, causing circuit resistance changes from the point of contact followed by a circuit potential switch to the other conducting layer for a second layer discharge changing the second layer circuit resistance, the two resistance changes representing the coordinate location of the contacting ball inside the sphere sensor and registering the ball location data in the logic for processing,
    whereby at the point of conducting layer contact, the voltage will be diverted from the x layer into the corresponding filament of the y layer revealing the y coordinate and reversing the discharge to obtain the x coordinate, analogous to a normal size flat touchscreen but with modifications to the spherical curvature and the small size.

2. The mini 3D spherical shaped orientation sensor device of claim 1, wherein the first conducting sheet layer has spacer dots coupled to an oxide conductive coating layered on a circuit layer supported on a glass or acrylic backing panel layer, facing the second conducting sheet layer having a conductive coating of Indium Tin Oxide or Antimonium Tin Oxide, adhering to an inside circuit layer coupled to polyethylene terephthalate film.

3. The mini 3D spherical shaped orientation sensor device of claim 1, further comprising an electrical alarm circuit which emits an aural alarm to the sensor wearer upon timer reaching a first pre-set time period.

4. The mini 3D spherical shaped orientation sensor device of claim 1, further comprising an electrical alarm circuit and component GPS sensor and autodialer, after a second pre-set time period, triggers an autodialer call for help to preset parties and sends GPS location and other rescue information via a wireless network.

5. The mini 3D spherical shaped orientation sensor device of claim 1, further comprising RFID tags emitting signals to an RFID reader coupled to the alarm circuit, upon sensor circuit energizing the RFID tags and causing the alarm circuit to receive the signal.

6. The mini 3D spherical shaped orientation sensor device of claim 1, further comprising and an added grid position circuit RFID tag which upon manual selection, turns off all individual sensor grid position circuits for a wearer sleep mode.

7. The mini 3D spherical shaped orientation sensor device of claim 1, wherein the two layer grid has variable grid point configuration.

8. The mini 3D spherical shaped orientation sensor device of claim 1, wherein the electrode conductor lines on substrates are either glass or plastic.

* * * * *